United States Patent
Taylor

(10) Patent No.: US 9,216,254 B2
(45) Date of Patent: Dec. 22, 2015

(54) MEDICAL TAPE

(71) Applicant: Ryan Taylor, Union City, NJ (US)

(72) Inventor: Ryan Taylor, Union City, NJ (US)

( * ) Notice: Subject to any disclaimer, the term of this patent is extended or adjusted under 35 U.S.C. 154(b) by 159 days.

(21) Appl. No.: 13/679,071

(22) Filed: Nov. 16, 2012

(65) Prior Publication Data

US 2013/0125900 A1    May 23, 2013

Related U.S. Application Data

(60) Provisional application No. 61/561,320, filed on Nov. 18, 2011.

(51) Int. Cl.
*A61F 13/00* (2006.01)
*A61M 5/32* (2006.01)

(52) U.S. Cl.
CPC ...... *A61M 5/321* (2013.01); *A61F 2013/00272* (2013.01); *A61F 2013/00387* (2013.01); *A61F 2013/00582* (2013.01); *A61F 2013/00587* (2013.01); *A61F 2013/00617* (2013.01)

(58) Field of Classification Search
CPC ..... A61F 13/00; A61F 13/02; A61F 13/0203; A61F 13/023; A61F 7/02; A61F 2013/0037; A61F 2013/00272; A61F 2013/00617; A61F 2013/00587; A61F 2013/00582; A61L 15/425; A61L 15/25; A61L 15/58
USPC ............... 602/41–59; 229/212; 128/846, 888; 2/455; 428/137
See application file for complete search history.

(56) References Cited

U.S. PATENT DOCUMENTS

| | | | | |
|---|---|---|---|---|
| 2,334,585 A * | 11/1943 | Schieman | ...... | 428/352 |
| 4,460,356 A | 7/1984 | Moseley | | |
| 4,858,245 A * | 8/1989 | Sullivan et al. | ...... | 2/21 |
| 4,942,626 A * | 7/1990 | Stern et al. | ...... | 2/161.7 |
| 4,966,138 A * | 10/1990 | Chow et al. | ...... | 602/57 |
| 5,507,079 A | 4/1996 | Schmidt et al. | | |
| 5,810,756 A | 9/1998 | Montecalvo et al. | | |
| 5,953,751 A | 9/1999 | Kobren | | |
| 5,984,088 A * | 11/1999 | Dietz et al. | ...... | 206/205 |
| 6,145,134 A * | 11/2000 | Davis et al. | ...... | 2/463 |
| 6,333,970 B1 * | 12/2001 | LeMaitre et al. | ...... | 378/162 |
| 7,148,160 B2 * | 12/2006 | Porter | ...... | 442/36 |
| 7,595,104 B2 * | 9/2009 | Romanowski | ...... | 428/40.1 |
| 7,960,603 B2 | 6/2011 | Evans | | |
| 2001/0016698 A1 | 8/2001 | Lloyd | | |
| 2001/0039401 A1 | 11/2001 | Ferguson et al. | | |
| 2002/0092529 A1 | 7/2002 | Rozier et al. | | |

(Continued)

FOREIGN PATENT DOCUMENTS

EP    878179 B1    4/2003
EP    1719613 A1 *    11/2006

(Continued)

*Primary Examiner* — Kim M Lewis
(74) *Attorney, Agent, or Firm* — Gearhart Law LLC

(57) ABSTRACT

An easy to use medical tape may have multiple layers including a first layer made of pressure absorbing materials such as flexible foam, and a needle resistant layer. The medical tape may further have a third layer made preferably of non-stick paper and a covering layer made preferably of vinyl. A medical professional making injections or performing an operation may cover his/her body or a patient's body with the medical tape to prevent needlestick injuries. Moreover, the medical tape may come in various shapes and sizes and may be cut into suitable pieces for different procedures.

10 Claims, 2 Drawing Sheets

(56) References Cited

U.S. PATENT DOCUMENTS

| | | |
|---|---|---|
| 2004/0065072 A1* | 4/2004 | Zhu et al. .................. 57/314 |
| 2004/0138602 A1 | 7/2004 | Rossen |
| 2005/0267410 A1 | 12/2005 | Koska |
| 2007/0027429 A1 | 2/2007 | Kuracina et al. |
| 2007/0105471 A1* | 5/2007 | Wang et al. ................ 442/301 |
| 2007/0299383 A1 | 12/2007 | Murphy et al. |
| 2008/0095979 A1* | 4/2008 | Hatanaka et al. ........... 428/137 |
| 2010/0173111 A1* | 7/2010 | Yamada ..................... 428/41.8 |
| 2011/0039082 A1 | 2/2011 | Yun et al. |
| 2011/0159225 A1* | 6/2011 | Boyle et al. ................ 428/41.8 |
| 2011/0168592 A1* | 7/2011 | Sakuragi .................... 206/366 |
| 2012/0298734 A1* | 11/2012 | Bradshaw et al. .......... 229/212 |
| 2013/0237790 A1* | 9/2013 | Riess et al. ................ 600/373 |

FOREIGN PATENT DOCUMENTS

| | | | |
|---|---|---|---|
| JP | 48048534 A | * | 6/1980 |
| WO | WO 91/12045 A1 | | 8/1991 |
| WO | WO 9211821 A1 | * | 7/1992 |
| WO | WO 00/20201 A1 | | 4/2000 |
| WO | WO 2010/038844 A1 | | 4/2010 |

* cited by examiner

MEDICAL TAPE

CLAIM OF PRIORITY

This application is a claims priority from U.S. provisional patent application 61/561,320, filed on Nov. 18, 2011, the contents of which are fully incorporated here by reference.

FIELD OF THE INVENTION

The invention relates to a multi-layered, easy-to-use medical tape, and more particularly to a medical tape that prevents injuries caused by needles, especially the needlestick injuries to healthcare professionals when they are trying to make an injection or perform a surgery. This invention also provides a device that holds a needle more firmly in place during surgery or infusion and folds over the needle once it has been removed from the patient while the needle is being transported and disposed.

BACKGROUND OF THE INVENTION

Needlestick injuries are common to healthcare workers, especially those who perform injections and surgeries regularly. According to data collected from 63 hospitals by the United States Occupational Safety & Health Administration (OSHA), the overall rate of needlestick injuries is 27 per 100 occupied beds annually. While nurses had the most frequent exposures (49.7 percent), physicians ranked second (12.6 percent). Such injuries are probably also frequent occurrences for non-professionals who take up the duty to perform injections in the course of taking care of himself/herself or a loved one. To simplify the description, the present application will refer mainly to healthcare professionals, while it should be clear that the invention will benefit anyone who may be subjected to medically related needlestick injuries.

In addition to the initial physical wounds, needlestick injuries can have serious consequences because the person injured may be exposed to pathogens or other contaminants that may result in grave secondary health risks. Such pathogens include but are not limited to: hepatitis B virus (HBV), hepatitis C virus (HCV), and human immunodeficiency virus (HIV). The danger that suffering a needlestick would induce infection is real and threatening to the healthcare professionals.

Besides the possibility of physical injuries and infections, a healthcare professional endures significant psychological pressure when he/she is concerned with needlestick injuries. The prospect that he/she might be injured may impair the concentration that is needed for the competent performance of a medical procedure. In addition to the psychological toll before injury, a person suffered from needlestick injury will be forced to endure the agonizing period waiting for test results as to whether a life-altering infection has occurred. The overall mental distress that may be caused by needlestick injuries is impossible to be ignored.

Being careful with needle and syringe operation can only help the person conducting an injection, infusion, or surgery to a certain extent. Sometimes it is inevitable that a slip of hand or occasional absentmindedness will occur and severe risks will result from a seemingly insignificant needlestick wound. The current invention helps to prevent needlestick injuries to healthcare professionals by providing a medical tape that cannot be penetrated in normal medical care operations. Nurses, physicians, and other healthcare workers can wear the medical tape at the necessary positions or apply the tape to certain locations that may subject the healthcare worker to possible needlestick injuries. With the tape properly worn or applied, the healthcare worker no longer needs to continue worrying about injuries and can focus on the task at hand.

Previous efforts to prevent needlestick injuries focus on using universal precautions, engineering and work practice controls, and personal protective equipments. The safety devices generally involve modifications to the syringes and needles, such as the following patent and patent publication:

European Patent EP 2331167A1 discloses an anti-needlestick system comprising a housing assembly. The assembly has a body portion. The body portion has distal and proximal ends, a cylindrical extent, and upper and lower sections. The distal end has a first aperture. The proximal end has a second aperture. The upper section has a lower edge and the lower section has an upper edge. A pair of flexible hinge portions is provided. The upper ends are coupled to the upper section. The lower ends are coupled to the lower section. The hinge portions are adapted to allow movement between closed and open orientations. Handling elements are formed with the main body portion. The handling elements include an upwardly extending projection located on the upper section essentially coplanar with the distal end to facilitate one handed utilization of the system.

U.S. Patent Publication No. US20050267410A1 discloses a needlestick prevention device for an injection device (1) having a hollow needle (2) comprises a sheath having a first member (9) for attachment to the injection device (1) and a second member (10) slidable longitudinally relative to the first member (9) to expose or to cover the needle (2), and spring means (11) biasing the second member (10) to cover the needle (2). The first and second members (9, 10) have inter-engaging guide means (13) and locking means (14), including a first guide part (23) operative to allow free longitudinal sliding movement of the second member (10) relative to the first member (9), and a second guide part (24) operative on movement by manual relative rotation of the first and second members (9, 10) and following release of a force urging the second member (10) to expose the needle (2). The spring means (11) urges the second member (10) to cover the needle (2) and to operate the locking means (14) to retain the second member (10) covering the needle (2). This allows free movement of the second member (10) in the first guide part (23), allowing for filling of the syringe (1), but then automatic sheathing and locking when the user simply twists the second member (10) relative to the first (9).

These modifications to needles or syringes are generally expensive and relatively more difficult to use. Moreover, they may not be appropriate for the specific medical procedure that is required for a particular patient. A more "defensive" approach may reduce such concerns. The healthcare professional may wear certain protective device on his/her hand that does not operate the needle or syringe. The following two patents serve as examples for such approaches.

U.S. Pat. No. 5,953,751 discloses a needlestick resistant glove for surgical and other medical uses including a flexible and elastic web which fits the user's hand. In one embodiment the web is partly covered by custom-fitted curved plates. The flexible web areas between the plates comprise hemispherical or disk protrusions. In another embodiment, without plates, the protrusions on the web are disks and the areas between the disks are covered by other disks.

U.S. Pat. No. 5,187,815 discloses a glove for use by medical personnel which is adapted to help prevent accidental injuries when handling needles includes a first discrete layer of flexible material which has a pore size smaller than the diameter of a needle. The first layer forms a glove with an optional opening in the fingerprint area of the index finger stall and middle finger stall. The glove also includes a second discrete layer of flexible material which also has a pore size which is smaller than the diameter of a needle. This second layer is permanently attached to selected areas of the first layer. The selected areas comprise all of the thumb stall, and lateral sides of the index finger stall and middle finger stall. Preferably, the fingernail region is not covered by the second layer and backsides of the first distal joint portion of the index and middle finger stall are covered. A V-opening for the back side of the glove includes two distinct fastening devices. A third discrete layer of corrugated metal foil is optionally provided in the selected areas. Methods for sterilization and disinfecting are also provided.

These inventions, however, are rather limited in another perspective because they both have gloves as embodiments but a glove cannot be worn on any other part of the body. While the hand not operating the needle may be subjected to possible injuries, other parts of the body can also be needle-sticked. The current invention addresses such inflexibility by introducing a needle-resistant medical tape that can be worn on any part of the body.

In conclusion, various implements are known in the art, but their structures are distinctively different from the current invention. Moreover, the prior art fails to address all of the problems solved by the invention described herein. One embodiment of this invention is illustrated in the accompanying drawings and will be described in more detail herein below.

SUMMARY OF THE INVENTION

As indicated above, needlestick injuries serve as a significant threat to the safety and welfare of the healthcare workers. Needlestick injuries can be caused by many kinds of injections, infusions, and operations. Accordingly, many kinds of needles, such as but not limited to syringe needles, infusion needles, and electrode needles, may cause needlestick injuries. The situations surrounding the injuries vary significantly. Some injuries involve errors in medical procedures; others may prove to be the result of a lack of protection. The most common needlestick injury may be caused by the mishandling of injections with a syringe needle. However, some injuries are caused by more exceptional incidents. One such example is the needlestick injuries that occur during spinal surgeries. In spinal surgeries, the healthcare professionals usually need to set up several electrode needles for monitoring the patient's neuronal activities. While these needles may cause injury to the healthcare worker when they are first being applied, they may cause further damages when they are dislodged from the patient's body, or even when movements in the surgery make the needles protrude out of the patient's skin. Since the electrode needles need to be affixed to the patients for a long time, the chances of needlestick injury in spinal surgeries are not infrequent.

The current invention discloses a medical tape that addresses the problem of needlestick injuries. The medical tape has a multi-layered structure that can protect a user of the medical tape from needlestick injuries. By wearing the medical tape at appropriate positions or applying the medical tape to likely places that might be subject to penetration, the healthcare work may prevent needlestick injuries and reduce the likelihood of secondary risks. Moreover, the medical tape disclosed here may serve multiple purposes besides blocking needlestick penetration. The medical tape is sticky on one side so that it may be used to fix an inserted fusion or surgery needle in place to prevent incidental dislodging and further injuries. In addition, the medical tape may be flexible enough to encapsulate a used needle before it is being disposed in a proper receptacle.

Various devices, apparatus, and mechanisms have been developed to reduce the likelihood of needlestick injuries. Since the medical tape described herein takes a defensive approach to needlestick injuries, there is no need to modify the structure of the needles or the apparatus applying the needles. Moreover, unlike the needlestick-proof gloves described above, the medical tape can be cut into any shape, applied anywhere, and used in a very flexible manner.

The medical tape disclosed in the current invention has a multi-layered structure, comprising a non-stick layer, a foam layer with a sticky side, at least one needle-resisting layer, and a top layer to provide additional resistance, comfort, coverage, color, and flexibility. The materials used for the medical tape are relatively inexpensive, making the medical tape affordable and boosting its availability. The specific material chosen for the needle-resistant layer may vary in a certain degree, allowing the medical tape to be available in different forms that may reflect the actually usage of the medical tape. The shape and size of the medical tape may vary, allowing it to be applied to different part of the body to fit different needs in injections, infusions, and operations.

It is an object of the present invention to provide a medical tape that reduces the needlestick injuries to healthcare professionals and other non-professional caregivers.

It is another object of the present invention to provide a medical tape that is easy to use and easy to put on and take off.

Yet another object of the present invention is to provide a medical tape that can be worn on any part of the user's body.

Still another object of the present invention is to provide a medical tape that allows the user to choose how much tape should be worn.

Yet another object of the present invention is to provide a medical tape that is inexpensive and disposable after use.

Still another object of the present invention is to provide a medical tape that is easily adjustable.

Yet another object of the present invention is to provide a medical tape that may fix an inserted needle in a patient's body.

Still another object of the present invention is to provide a medical tape that may be wrapped around a needle before it is being disposed.

Still another object of the present invention is to provide a medical tape that is multiple layered and protects the user from injuries that can be caused by different kinds of needles.

DESCRIPTION OF THE PREFERRED EMBODIMENTS

Figure 1:
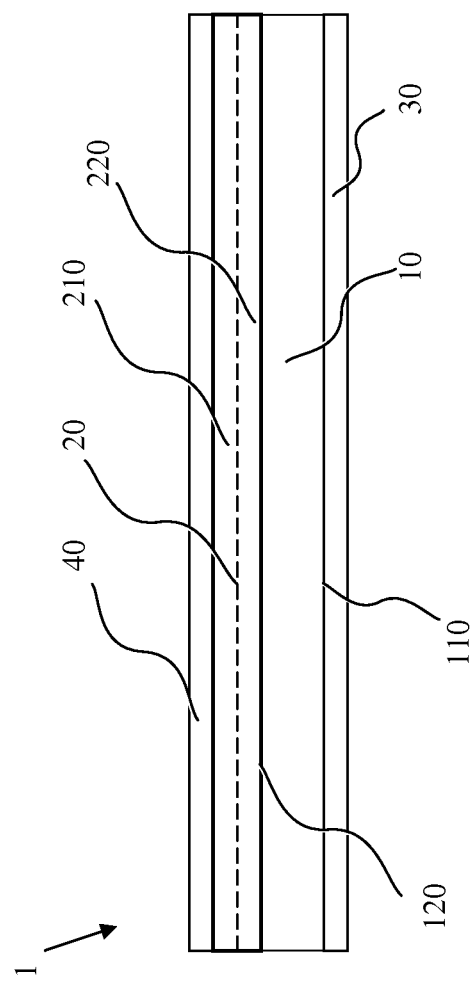
FIG. 1 is a cross section view of a preferred embodiment of the medical tape.

The preferred embodiments of the present invention will now be described with reference to the drawings. Identical elements in the various figures are identified with the same reference numerals.

Reference will now be made in detail to embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a cross section view of a preferred embodiment of the medical tape, which has multiple layers. Shown is the medical tape 1 having a first layer 10 having a first side 110 and a second side 120; a second layer 20 having a first sub-layer 210 and a second sub-layer 220, which is needle resistant, a third layer 30 and the top covering layer 40.

To show the different layers more clearly, the thickness of the layers shown in FIG. 1 is not proportional. Generally, the medical tape 1, as a whole, should not be too thick to prevent smoothly conducting the procedures that are needed. While the thickness of the first layer 10 may be 0.1 to 10 millimeters (mm), the overall thickness of the second layer may be 0.1-5 mm. In the preferred embodiment, while the first layer 10 is about 1.59 mm (1/16 inch) thick, the first sub-layer 210 of the second layer 20 is about 0.19 mm (0.0075 inch) thick, and the second sub-layer 220 of the second layer 20 is also about 0.19 mm (0.0075 inch) thick. It should be noted that as long as the thickness of the layers does not prevent the effective blocking of most of the common needlestick penetrations, the thickness is acceptable.

The first layer 10 provides a soft touch for the medical tape 1, allowing the tape to be worn comfortably. In certain circumstances, the first layer 10 may also absorb pressure and reduce the likelihood that a needle will penetrate the medical tape 1. The first layer 10 has a first side 110 and a second side 120. The first side 110 is designed to be sticky and may attach to the skin of a patient or any other surfaces that may need protections. In the preferred embodiment, the adhesive used for the first side 110 is acrylic. However, it should be noted that any adhesive is acceptable as long as it is non-toxic and the medical tape 1 can be attached firmly and removed without harming the patient. When the medical tape 1 is not in use, the first side 110 of the first layer 10 is attached to the third layer 30. The third layer 30 of the medical tape 1 may be made from non-sticky paper, allowing the medical tape 1 to be handled without attaching to its surroundings before the medical tape 1 is in use. The third layer 30 may be removed before the medical tape 1 is applied so that the first side 110 of the first layer 10 is exposed and the medical tape 1 may be attached to any desirable site.

Since the first side 110 is sticky, the medical tape 1 may be used to fix an inserted needle to a patient's body. During an infusion or some particular surgery, such as the spinal surgery using electrode needles, there is a need to assure that the inserted needle to stay in place, most often for a long period of time, such as several hours. The medical tape 1, in such circumstance, may serve to fix the needle in place by being taped to the hold part of the needle to the skin, not allowing it to slip out of its intended anatomical position. Furthermore, the medical tape 1 may protect the patient and staff while the patient is being moved, transported, or restrained.

Though the first layer 10 does not need to be completely needle resistant, it may reduce the power of penetration when a needlestick protrusion is applied to it, helping to reduce the chances of injury. In spinal surgeries, for example, the electrode needles that are attached to a patient's body may penetrate the patient's skin and cause injury to the healthcare professional. If the medical tape 1 is applied to the patient's skin, the first layer 10 may be the first line of defense against a possible penetration. The first layer 10, therefore, serves to provide the initial blockade to needlestick penetration by reducing the needle's force.

The first layer 10 may be made from soft and flexible material that may absorb pressure. A preferred material is flexible foam, such as Polyurethane. In the preferred embodiment, the first layer 10 is made from polyurethane foam tape provided by 3M, Inc. Aside from flexible foam, the first layer 10 may be made from many kinds of materials such as flexible plastic, including but not limited to Ethylene Vinyl Acetate (EVA), flexible PVC, High Density Polyethylene (HDPE), Expanded Polypropylene (EPP), and Ethylene Vinyl Acetate (EVA). As long as the material is non-toxic, flexible, and pressure absorbing, it may be made into the first layer 10.

The second layer 20 is the needle-resistant layer of the medical tape 1. While the first layer 10 may reduce the pressure from a protruding needlestick, the second layer 20 may serve as the main blockade to stop the needlestick from penetration. The second layer 20 is tightly attached to the first layer 10, with a method that may vary according to the materials used to make the first layer 10 and second layer 20. For example, the first layer 10 and second layer 20 may be glued, molded, or co-molded to ensure close attachment.

While FIG. 1 shows the second layer 20 to be a two-layered structure having the first sub-layer 210 and the second sub-layer 220, it should be noted that the needle-resistant second layer 20 may be one single layer or a combination of a number of sub-layers. A single layer structure is generally easier for manufacturing purposes. However, a multi-layered design may enhance the capacity of the second layer 20 to block needlestick penetrations. The sub-layers of the second layer 20 may be glued, molded, or co-molded to ensure close attachment.

The second layer 20 may be made from flexible, semi rigid, or rigid plastic or other materials that are needle resistant. In the preferred embodiment, the second layer 20 is made of fabrics or sheets based on steel core yarn technology, such as the Rhinoguard™ material manufactured by Tilsatec. The Rhinoguard™ material is composed of proprietary coating(s) with aramid materials, and is rated to safely deflect needles and other puncture probes by the American Society for Testing and Materials (ASTM). The ASTM is an international standards organization that develops technical standards for a wide variety of materials. One such standard Is the testing method for protective clothing's material resistance to puncture (see ASTM F1342-05). Under this testing method, the Rhinoguard™ material withstood 86 Newtons (N) of force from a standard 2.03 millimeter (mm) puncture probe, Under the modified test, the Rhinoguard™ material withstood 4.1N for a sharpened 25 gauge medical grade needle.

Moreover, other materials that may be used include but are not limited to: fiber composite fabrics such as the Turtle-Skin® material, silicone, wood, high density rubber, sheet metal such as aluminum, Polyethylene terephthalate (PET) ABS, Polycarbonate, Noryl™, PVC, Polystryrene, ABS/PVC, PVC/Acrylic, Polysulfone, Acrylic, Polyethylene, and Kydex™. Other materials that may be used to make the second layer 20 include high density fabrics or joint sheets with special coating as blocking elements. One alternative material is the SuperFabric® material that is needle-resistant and flexible. The key requirement for the material to make the second layer 20 is it must be needle resistant and can be easily molded into different thickness, sizes, and shapes.

The sub-layers of the second layer 20 may be made of same of different materials. For example, two different kinds of materials, such as steel core yarn sheets, PET and SuperFabric®, may be used to make the two sub-layers that combine to form the second layer 20. Nevertheless, the sub-layers may be made from the same material. The second layer 20 preferred embodiment shown in FIG. 1 has two sub-layers 210 and 220 that are both made of PET. As long as the sub-layers are tightly attached and work to block needlestick penetration, the choice of materials may be rather flexible.

Figure 2B:
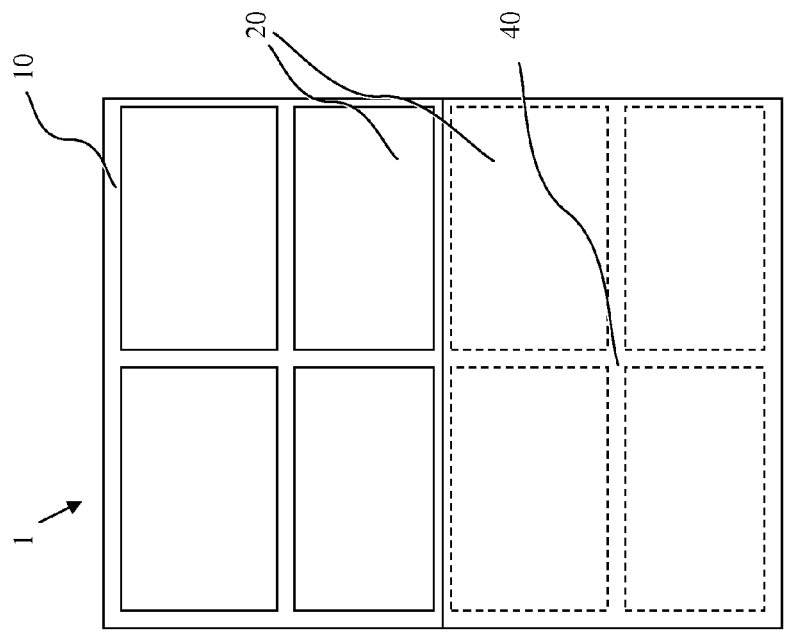
FIG. 2B is a top cut-away view of another embodiment of the medical tape.
Figure 2A:
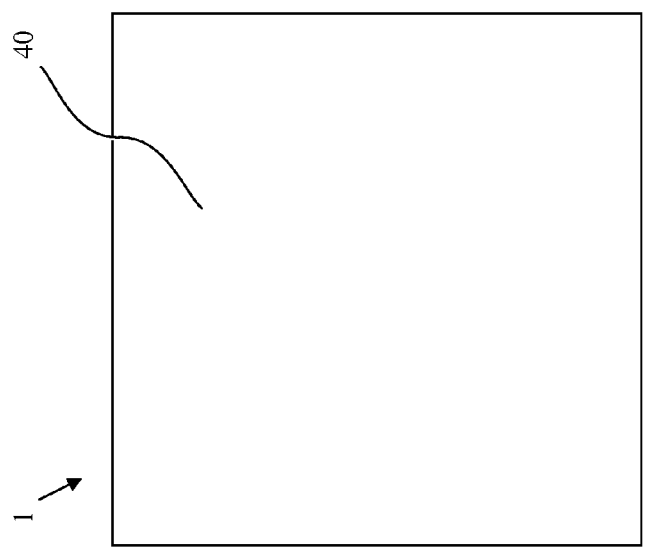
FIG. 2A is a top view of a preferred embodiment of the medical tape.

FIGS. 2A and 2B show a top view of two preferred embodiments of the medical tape 1. In FIG. 2A, the medical tape 1 is shown as a rectangular shape, while the only visible portion is a top covering layer 40. All the other layers are the same size as the covering layer 40. FIG. 2B is a top cut-away view that shows the medical tape 1 having the top covering layer 40, the second needle-resistant layer 20, and the first layer 10. The covering layer 40 is made partially transparent to make the first layer 10 and second layer 20 visible.

The medical tape 1 may be provided as different shapes. The most common shape is what is shown in FIGS. 2A and 2B, as square or rectangular pieces. However, the medical tape 1 may be made to be round, oval, triangular, or any other shape that might fit the needs for a specific operation. As an example, the medical tape 1 may be in a butterfly shape that may be suitable for attachable to the fingers or the palm edge of a user.

The medical tape 1 may be provided as different sizes. In general, since the medical tape 1 may be cut into smaller pieces or a few tapes may be aligned to provide bigger coverage, the size of the medical tape 1 may be flexible. In particular, the square medical tape 1 shown in FIG. 2A has a size of 5.08 cm (2 inches) by 5.08 cm (2 inches). As long as it fits the requirement of the medical procedure that is being performed, the medical tape 1 may be any size that is practical.

While FIG. 2A shows all the layers of the medical tape 1 to be the same size and shape, and being arranged in a completely overlapping format, it should be noted that the different layers may be somewhat different in their parameters to facilitate the application of the medical tape 1. Take FIG. 2B as an example, the second layer 20 is not a complete big piece. In a top cut-away view, FIG. 2B shows the second layer 20 being divided into smaller patches than the first layer 10 and the covering layer 40. In FIG. 2B, the second layer 20 is arranged in rectangular patches that still covers the vast majority of the overall area. Such a design allows easier bending and cutting of the medical tape 1 because second layer 20, compared with the other layers, is less flexible and more difficult to cut. The arrangement is necessary especially when the second layer 20 is made of rigid material such as Polycarbonate. This design, however, only minimally impacts the capacity of the medical tape 1 to block needlestick penetration because the needle-resistant second layer 20 still covers more than 90% of the entire medical tape 1.

Overall, the medical tape 1 is preferred to be flexible and may be easily wrapped around an object. The contributing factors include what material the second layer 20 is made of and how the second layer 20 is arranged. By adopting a fragmented format for the second layer 20, the medical tape 1 may be flexible even if the material making the second layer 20 is rigid. Nevertheless, plenty of materials, such as the SuperFabric®, may ensure that the medical tape is both needle resistant and flexible.

Being flexible allows the medical tape 1 to serve another purpose. When an infusion or a surgery is completed, the medical tape 1 may be wrapped around the needle that is no longer needed and prevent accidental injuries. The medical professional may take the needle encapsulated in the medical tape 1 and dispose the needle in a proper receptacle, without worrying about incidental injuries during the transporting and disposal processes.

As shown in FIGS. 1 and 2, the medical tape 1 may comprise a top covering layer 40. The top covering layer 40 may be directly attached to the second layer 20. The top covering layer 40 provides coverage, comfort and/or stability. In one embodiment, the covering layer 40 may serve the same function as the first layer 10, absorbing pressure and reducing the likelihood that a needle will penetrate the medical tape 1. The top covering layer 40 may be made from any material that is flexible and can be made into a thin layer. In the preferred embodiment, the covering layer 40 may be made from polyurethane foam. Aside from flexible foam, the first layer 10 may be made from many kinds of materials such as flexible plastic, including but not limited to Ethylene Vinyl Acetate (EVA), flexible PVC, High Density Polyethylene (HDPE), Expanded Polypropylene (EPP), and Ethylene Vinyl Acetate (EVA). As long as the material is non-toxic, flexible, and pressure absorbing, it may be made into the first layer 10.

It is also preferred that the top covering layer 40 is able to receive printing or marking. In one preferred embodiment, the top covering layer 40 may have color and may be printed or inscribed. On the top covering layer 40, a manufacturer of the medical tape 1 may print a logo, a sign, a warning, or any content that is proper. For example, a warning to prevent needlestick injuries can be printed to alert the medical professional to stay focused during a procedure. In addition, the color and inscriptions on the top covering layer 40 may provide distinctions between different types of medical tapes suitable for different procedures, ensuring that the most effective medical tape 1 is used.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A medical tape, comprising:
    a first layer made of flexible foam, the first layer having a first sticky side and a second side;
    a second layer made from steel core yarn and attached to the second side of the first layer;
    a third layer made of non-stick paper attached to the first side of the first layer; and
    a covering layer made of flexible foam attached to the second layer.

2. The medical tape of claim 1, wherein the first layer has a thickness of about 1.59 millimeters.

3. The medical tape of claim 1, wherein the covering layer has a color and an indicium inscribed on the covering layer.

4. A needle resistant tape comprising:
    a first layer comprising a polyethylene foam having a first side and a second side with the first side having an adhesive disposed thereon;
    a second layer having a first sub-layer and a second sub-layer with at least one sub-layer comprising a steel core yarn,
    wherein the second layer is attached to the first layer;
    a third layer made of non-stick paper removably attached to the first side of the first layer; and
    a flexible foam layer covering and attached to the second layer.

5. The needle resistant tape of claim 4 wherein the tape resists up to about 85N from a standard 2.03 mm puncture probe in accordance with the ASTM F1342-05 test and about 4N from a 25 gauge sharpened medical grade needle using the modified ASTM F1342-05 test.

6. The needle resistant tape of claim 4 wherein the needle resistant material comprises coated aramid fibers or steel core yarns or any combination thereof.

7. The needle resistant tape of claim 4 wherein the second side of the first layer is attached to the second layer.

8. The needle resistant tape of claim 4 wherein the adhesive is an acrylic.

9. The needle resistant tape of claim 4 wherein the flexible foam layer covering and attached to the second layer alerts the user to the presence of needles by way of color, symbols, lettering, words, or any combination thereof.

10. The medical tape of claim 4, wherein the first sub-layer is comprised of the steel core yarn and the second sub-layer is independently comprised of steel core yarn, Polyethylene terephthalate (PET), fiber composite fabrics, silicone, wood, high density rubber, sheet metal such as aluminum, ABS, Polycarbonate, polyphenylene ether, PVC, Polystyrene, ABS/PVC, PVC/Acrylic, Polysulfone, Acrylic, Polyethylene, Acrylic/PVC, or coated or uncoated aramid fibers.

* * * * *